United States Patent
Park (10) Patent No.: US 9,684,022 B2
(45) Date of Patent: Jun. 20, 2017

(54) SENSOR DEVICE AND SENSING METHOD USING THE SAME

(71) Applicant: ELSSEN, Daejeon (KR)

(72) Inventor: Ji Man Park, Daejeon (KR)

(73) Assignee: ELSSEN, Daejeon (KR)

( * ) Notice: Subject to any disclaimer, the term of this patent is extended or adjusted under 35 U.S.C. 154(b) by 53 days.

(21) Appl. No.: 14/751,528

(22) Filed: Jun. 26, 2015

(65) Prior Publication Data

US 2016/0370410 A1 Dec. 22, 2016

(30) Foreign Application Priority Data

Jun. 22, 2015 (KR) .................. 10-2015-0088678

(51) Int. Cl.
| | |
|---|---|
| *G01R 19/252* | (2006.01) |
| *G01R 27/26* | (2006.01) |
| *G01R 27/02* | (2006.01) |
| *A61B 5/0428* | (2006.01) |
| *H03M 1/00* | (2006.01) |

(52) U.S. Cl.
CPC ........ *G01R 27/2605* (2013.01); *A61B 5/0428* (2013.01); *G01R 27/02* (2013.01); *H03M 1/00* (2013.01)

(58) Field of Classification Search
CPC ............................ G01R 19/252; G01R 19/165
USPC ......................................................... 324/676
See application file for complete search history.

(56) References Cited

U.S. PATENT DOCUMENTS

| | | | | |
|---|---|---|---|---|
| 6,535,192 B1* | 3/2003 | Sung | .................... | G09G 3/2011 345/94 |
| 2007/0008100 A1* | 1/2007 | Qi | .......................... | G05B 11/28 340/506 |
| 2010/0011856 A1* | 1/2010 | Nagata | .................... | G01C 19/56 73/504.12 |
| 2013/0312516 A1* | 11/2013 | Pyo | .................... | G01C 19/5776 73/504.02 |

FOREIGN PATENT DOCUMENTS

| | | |
|---|---|---|
| JP | 2006333203 | 12/2006 |
| KR | 1020140139857 | 12/2014 |

* cited by examiner

*Primary Examiner* — Son Le
*Assistant Examiner* — Akm Zakaria
(74) *Attorney, Agent, or Firm* — Novick, Kim & Lee, PLLC; Sang Ho Lee

(57) ABSTRACT

Provided are a sensor device and a sensing method using the same. The sensor device according to the present invention includes: a sensing voltage generating unit outputting different voltage values depending on an external environment; a pulse generating unit generating a pulse having a period which is proportional to an input voltage; a divider dividing an output of the pulse generating unit; and a counter unit measuring a length of an output pulse of the divider in a clock unit. As a result, the sensor device including an analog-digital converter (ADC) using a pulse width modulation technology is a miniature device and has high resolution.

1 Claim, 6 Drawing Sheets

SENSOR DEVICE AND SENSING METHOD USING THE SAME

CROSS-REFERENCE TO RELATED APPLICATIONS

This application claims priority under 35 U.S.C. §119 to Korean Patent Application No. 10-2015-0088678, filed on Jun. 22, 2015, in the Korean Intellectual Property Office, the disclosure of which is incorporated herein by reference in its entirety.

TECHNICAL FIELD

The following disclosure relates to a sensor device and a sensing method, and more particularly, to a sensor device including a miniature and high resolution analog-digital converter (ADC), and a sensing method using the same.

BACKGROUND

Various sensor devices have been used for various technology fields, and in order to convert a sensor measurement value into a digital signal, an analog-digital converter (ADC) is required.

A pulse width modulation technology (a method using a pulse width modulator), which is one of ADC technologies according to the related art, has several advantages. However, since a pulse width may not be increased when being implemented in a chip, it is difficult to increase resolution. That is, a value of a capacitor is decreased to implement the pulse width modulation technology in a miniature chip, wherein if amplitude of a charged current is excessively decreased to increase the pulse width, the current becomes sensitive to noise. Therefore, it is also impossible to decrease a value of the current to a predetermined value or less. As a result, the pulse width may not be increased to a predetermined value or more, and it is also difficult to increase the resolution.

SUMMARY

An embodiment of the present invention is directed to providing a sensor device including an ADC using a pulse width modulation technology capable of having high resolution even in a miniature device, and a sensing method using the same.

In one general aspect, a sensor device includes: a sensing voltage generating unit 10 outputting different voltage values depending on an external environment; a pulse generating unit 30 generating a pulse having a period which is proportional to an input voltage value; a divider 40 dividing an output of the pulse generating unit 30; and a counter unit 50 measuring a length of an output pulse of the divider 40 in a clock unit.

The sensor device may further include: a sample and hold (S/H) unit 20 sampling and holding an output voltage value of the sensing voltage generating unit 10.

The sensor device may include two or more S/H units 20, pulse generating units 30, dividers 40, and counter units 50, and the sensing voltage generating unit 10 may be connected to the two or more S/H units 20 and output voltages of the respective S/H units 20 may be connected to the pulse generating units 30, the dividers 40, and the counter units 50 which are different from each other, such that a parallel processing of a voltage sense may be enabled.

The pulse generating unit 30 may include a capacitor, a current source, a switch, and a comparator.

The sensor device may further include a circuit removing components except for a pulse width of the output of the pulse generating unit 30 from the output pulse of the divider 40.

The divider 40 may be a $2^n$ divider.

In another general aspect, a sensing method using a sensor device including a sensing voltage generating unit 10, a pulse generating unit 30, a divider 40, and a counter unit 50 includes: a first operation of outputting, by the sensing voltage generating unit 10, different voltage values depending on an external environment; a third operation of generating, by the pulse generating unit 30, a pulse having a period which is proportional to an input voltage value; a fourth operation of dividing, by the divider 40, an output of the pulse generating unit 30; and a fifth operation of measuring, by the counter unit 50, a length of an output pulse of the divider 40 in a clock unit.

The sensing method may further include: between the first operation and the third operation, a second operation of storing and then outputting, by an S/H unit 20, a voltage value of a specific instant of an output voltage of the sensing voltage generating unit 10.

In the fourth operation, a process of dividing the output of the pulse generating unit 30 by twice may be repeated n times (n is an integer).

DETAILED DESCRIPTION OF EMBODIMENTS

Since the present invention may be variously modified and have several exemplary embodiments, specific exemplary embodiments will be shown in the accompanying drawings and be described in detail in a detailed description. However, it is to be understood that the present invention is not limited to the specific exemplary embodiments, but includes all modifications, equivalents, and substitutions included in the spirit and the scope of the present invention. When it is determined that the detailed description of the known art related to the present disclosure may obscure the gist of the present disclosure, the detailed description thereof will be omitted.

Terms used in the present specification are used only in order to describe specific exemplary embodiments rather than limiting the present invention. Singular forms used herein are intended to include plural forms unless explicitly indicated otherwise.

Figure 1:
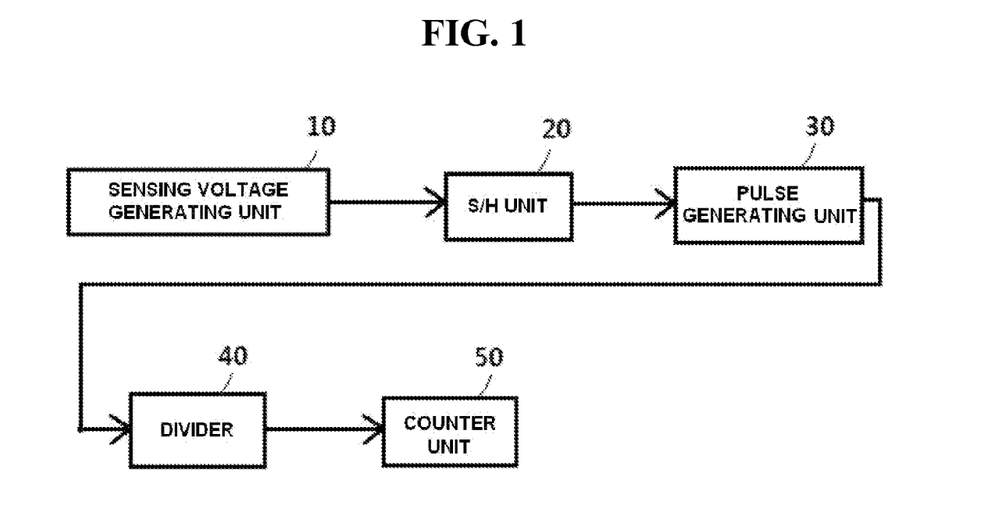
FIG. 1 is a conceptual view of a sensor device according to the present invention.

FIG. 1 is a configuration diagram of a sensor device according to the present invention.

The sensor device according to the present invention includes a sensing voltage generating unit 10, an S/H unit 20, a pulse generating unit 30, a divider 40, and a counter unit 50.

The sensing voltage generating unit 10 outputs different voltage values depending on an external environment.

The S/H unit 20 serves to sample and hold the output voltage value of the sensing voltage generating unit.

The pulse generating unit 30 generates a pulse having a period which is proportional to the output voltage value of the S/H unit 20.

The divider 40 serves to divide an output of the pulse generating unit 30.

The counter unit 50 measures a length of an output pulse of the divider 40 in a clock unit.

In this case, as a dividing ratio of the divider 40 is increased, resolution is improved.

The sensing voltage generating unit 10 may be implemented in various forms. A scheme which is widely used in the sensor according to the related art is to use an element of which resistance is changed or capacitance is changed depending on the external environment (e.g., temperature, humidity, or the like). When a predetermined current flows in the element of which resistance is changed, a voltage is changed depending on the external environment. When the predetermined current flows in the element of which capacitance is changed depending on the external environment, an increase rate of the voltage is changed depending on the external environment. When a predetermined voltage is applied to the element of which capacitance is changed depending on the external environment, an amount of current is changed depending on the external environment, and when the current flows through a resistor, magnitude of the voltage across the resistor is changed.

Since a technology of changing the output voltage depending on the external environment is known in the related art, a detailed description thereof will be omitted.

Since an output of the element is generally very weak so that the output voltage is changed depending on the external environment, an amplifier may also be used. The amplifier may be selected to be used among various kinds of amplifiers (e.g., a voltage-voltage amplifier, a current-voltage amplifier, a voltage-current amplifier, etc.) according to a design need. The amplifier is used because a signal by the external environment is weak. Therefore, if the signal has a large value even in the case in which the amplifier is not used, the amplifier is not required.

In addition, the sensing voltage generating unit 10 may additionally include a filter circuit, and in the case in which there is no noise in the signal by the external environment, the filter circuit is not required.

In the sensor according to the related art, the sensing voltage generating unit 10 generally uses the element of which resistance is changed or capacitance is changed depending on the external environment (e.g., temperature, humidity, or the like), but may also generate a sensing voltage value of the external environment without using the above-mentioned element. For example, in the case in which an electrocardiogram is measured, if an electrode is just connected to a point from which an electrocardiogram voltage may be obtained, the electrocardiogram may be operated as the sensing voltage generating unit 10. In this case, since the signal of the sensing voltage generating unit 10 may be very weak, the sensing voltage generating unit 10 may preferably include the amplifier.

Figure 2:
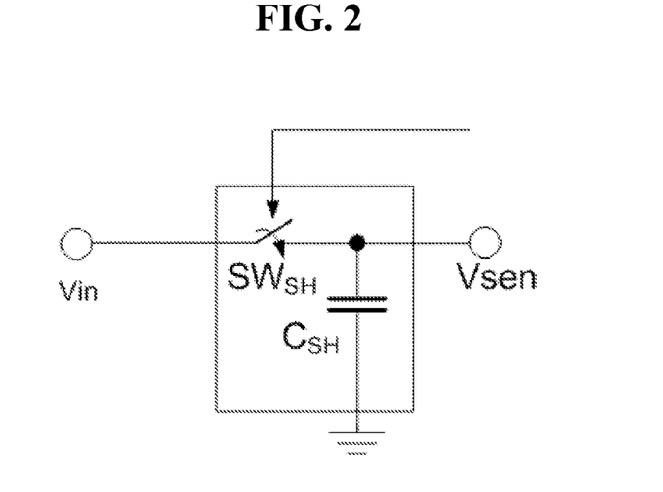
FIG. 2 is a configuration diagram of an S/H unit.

FIG. 2 is a configuration diagram of an S/H unit.

The S/H unit 20 is a sample and hold circuit that samples and holds an input voltage.

When a switch $SW_{SH}$ of the S/H unit 20 is closed, a voltage of capacitance $C_{SH}$ is equal to an input voltage Vin, but when the switch $SW_{SH}$ of the S/H unit 20 is opened, the voltage of capacitance $C_{SH}$ is held at a value of an instant at which the switch $SW_{SH}$ is opened.

Since the output voltage at this point is a voltage value obtained by sensing a surrounding environment, this may be referred to as Vsen in view of a sensing voltage.

Since the output of the sensing voltage generating unit 10 may contain noise, it is preferable to install a filter circuit.

The filter circuit that removes the noise may also be installed between the sensing voltage generating unit 10 and the S/H unit 20, and the filter circuit that removes the noise may also be installed between the S/H unit 20 and the pulse generating unit 30.

In the sensor device according to the present invention, in the case in which the input voltage of the S/H unit 20 is not changed for a predetermined time or more, the S/H unit 20 may be removed.

Figure 3:
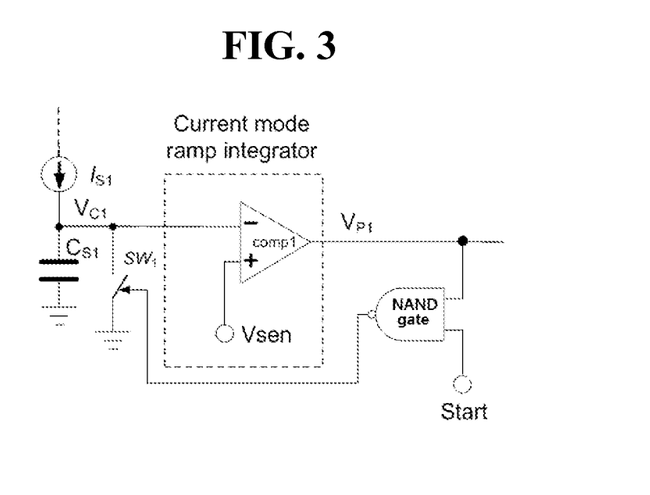
FIG. 3 is a configuration diagram of an example of a pulse generating unit.

FIG. 3 is a configuration diagram of an example of the pulse generating unit.

The pulse generating unit of FIG. 3 includes a capacitor $C_{S1}$, a current source $I_{S1}$, a switch $SW_1$, a comparator comp 1, and a NAND gate.

The comparator comp 1 may be implemented in an operational (OP) amplifier.

One end of the capacitor $C_{S1}$ is grounded and the other end thereof is connected to the current source $I_{S1}$. The switch SW1 is connected in parallel to the capacitor $C_{S1}$. A positive (+) input of the comparator comp 1 is connected to Vsen (the output voltage of the S/H unit), and a negative (−) input of the comparator comp 1 is connected to a connection point between the capacitor $C_{S1}$ and the current source $I_{S1}$.

An output of the comparator comp 1 and a start signal become an input of the NAND gate, and when an output of the NAND gate becomes a high state, the switch SW1 is closed.

When a start value is in a low state, an output value of the NAND gate becomes the high state, which causes the switch SW1 to be closed. Therefore, the pulse generating unit of FIG. 3 is not operated.

If the start value is changed to the high state, the output value of the NAND gate becomes the low state, which causes the switch SW1 to be opened.

In the state in which the switch SW1 is opened, an amount of charges stored in the capacitor $C_{S1}$ by the current source $I_{S1}$ is increased, and as the amount of charges stored in the capacitor $C_{S1}$ is increased, a voltage $V_{C1}$ of the capacitor $C_{S1}$ is increased.

If $V_{C1}$ is increased to be larger than Vsen, an output voltage $V_{P1}$ of the comparator comp1 is reversed from the high state to the low state.

If $V_{P1}$ is changed from the high state to the low state, the output value of the NAND gate becomes the high state, which causes the switch SW1 to be closed. If the switch SW1 is closed, the voltage $V_{C1}$ of the capacitor $C_{S1}$ again becomes zero, and $V_{P1}$ is reversed from the low state to the high state.

If $V_{P1}$ is changed to the high state, the output value of the NAND gate becomes the low state, which causes the switch $SW_1$ to be opened.

That is, $V_{P1}$ is repeated between the low state and the high state, wherein a width and period of a pulse is proportional to magnitude of Vsen.

The same operation is performed even in the case in which the NAND gate of FIG. 3 is exchanged with an AND gate and the switch SW1 is configured to be opened when an output value of the AND gate is in the high state.

It is preferable to have a predetermined delay time or more by additionally installing a buffer in the output of the NAND gate.

Although FIG. 3 illustrates the case in which the Vsen value is input to the positive (+) input of the comparator, the circuit may also be modified so that the Vsen value is input to the negative (−) input of the comparator.

In this case, since the value of $V_{C1}$ is increased in a ramp shape, the circuit of FIG. 3 (the circuit including the comparator) may be referred to as a current mode ramp integrator.

Since the pulse width of $V_{P1}$ is proportional to the magnitude of Vsen, the magnitude of Vsen may be known by measuring the pulse width.

When the magnitude of Vsen is determined with a method for determining how many clock periods are equal to the pulse width, it is preferable to have the pulse width which is much larger than the clock period in order to increase resolution of Vsen.

However, there is a limit in decreasing the clock period, that is, increasing a clock frequency. The reason is that if the clock frequency is excessively increased, there are problems that power consumption is increased and a malfunction risk is increased.

In addition, the capacitance of the capacitor $C_{S1}$ needs to be increased or the current value of the current source $I_{S1}$ needs to be decreased in order to increase the pulse width of $V_{P1}$, but there are problems that if the capacitance is increased, a size of the capacitor $C_{S1}$ is increased, which may prevent miniaturization of the device, and if the current value of the current source $I_{S1}$ is decreased, the device becomes vulnerable to noise.

In order to solve the above-mentioned problems, according to the present invention, the pulse width is increased by passing the output of the pulse generating unit 30 through the divider 40.

Figure 4:
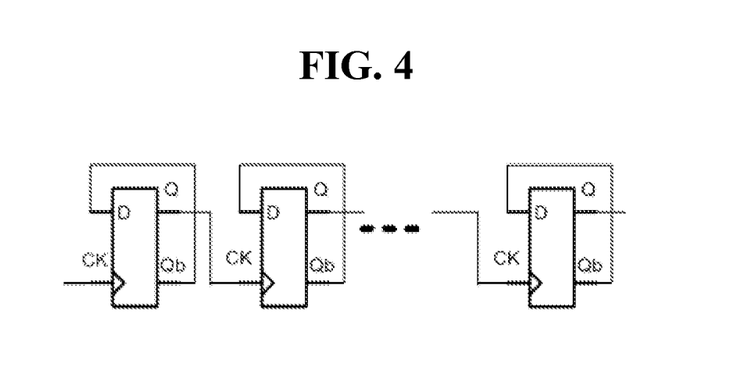
FIG. 4 is a configuration diagram of an example of a divider.

FIG. 4 is a configuration diagram of an example of the divider.

The divider 40 may be implemented in several schemes, but in the divider of FIG. 4, a plurality of D flip-flops are connected in series with each other and an output Qb of each D flip-flop is connected to an input D, such that when a state of an input CK is changed twice, a state of an output Q is changed once.

In the case in which n D flip-flops of FIG. 4 are connected in series with each other, since the number of state change times of the input is changed to be decreased by $2^n$ times, the divider may be called a $2^n$ divider.

The divider 40 according to the present invention, which is a circuit that decreases the number of state change times of the inputs at a predetermined ratio, may be modified in various forms in addition to the form shown in FIG. 4 according to a design need.

The divider 40 of FIG. 4 is configured by connecting a plurality of circuits each of which is divided by twice in series with each other, but the circuit may also be theoretically divided by not twice but integer times (e.g., three times, ten times, or the like). However, since the circuit is simple and is most efficient when being divided by twice, it is preferable to connect the plurality of circuits each of which is divided by twice in series with each other as shown in FIG. 4.

Figure 5:
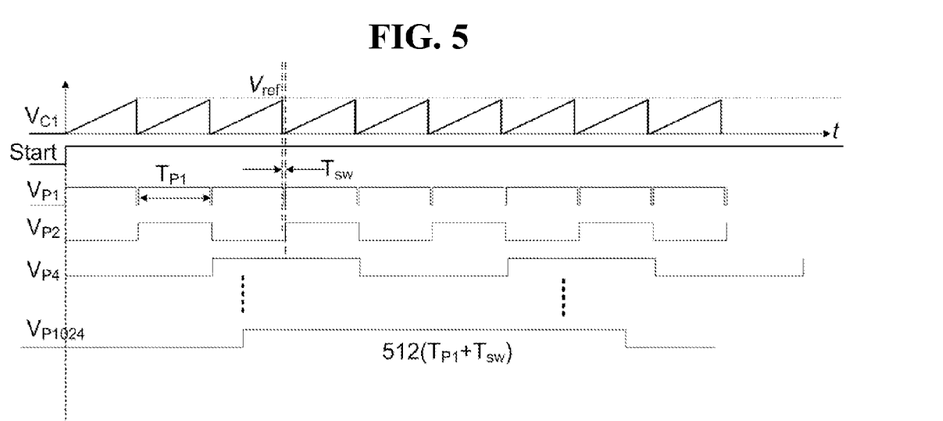
FIG. 5 is a voltage graph in circuits of FIGS. 3 and 4.

FIG. 5 is a voltage graph in the circuits of FIGS. 3 and 4.

That is, FIG. 5 is a graph obtained by comparing voltage values of several points of the circuits when the circuit of FIG. 3 and the circuit of FIG. 4 are connected to each other.

$T_{P1}$ is a time during which $V_{P1}$ is in the high state, and $T_{SW}$ is a time during which $V_{P1}$ is the low state.

If the start value is changed to the high state, $V_{P1}$ is regularly changed while having the pulse width of $T_{P1}$ and a period of $T_{P1}+T_{SW}$.

$V_{C1}$ is increased until $V_{C1}$ reaches a $V_{ref}$ value, wherein the $V_{ref}$ value in FIG. 5 is equal to the Vsens value.

Since the pulse width and period are generally increased by twice whenever $V_{P1}$ passes through the D flip-flop of FIG. 4, values after $V_{P1}$ passes through one D flip-flop may be each referred to as $V_{P2}, V_{P4}, \ldots, V_{P1024}$.

Since a pulse width $512(T_{P1}+T_{SW})$ of $V_{P1024}$ has high resolution due to a wide pulse width and is a value which is increased so as to be proportional to the Vsen value, the Vsen value may be measured with high resolution in the case in which it is determined how many clocks correspond to the pulse width of $V_{P1024}$.

The counter unit 50, which is a circuit determining how many clocks correspond to a width of an output pulse of the divider 40, may be implemented by several methods.

A simplest method for implementing the counter unit 50 is a method in which a counting circuit (a circuit in which an output value of N bits is increased by 1 whenever a clock input is changed) receives the output value of the divider 40 as an enable input of the counting circuit. In the case in which the circuit is implemented as described above, since the counting circuit is operated only when the output value of the divider 40 is in the high state, it may be measured how many clocks correspond to the pulse width of the output value of the divider 40. If the above-mentioned method is applied, a process in which a value of the counting circuit is initialized to zero when a pulse to be measured is changed to the high state is required.

A detailed circuit of the counter unit 50 may be variously changed according to the design need.

In addition, the examples shown in FIGS. 3 and 4 may be performed so as to be changed to a form in which unnecessary time factors (a switching time and a clock delay time) are calculated so as to be removed from the pulse width of the divider.

Figure 6:
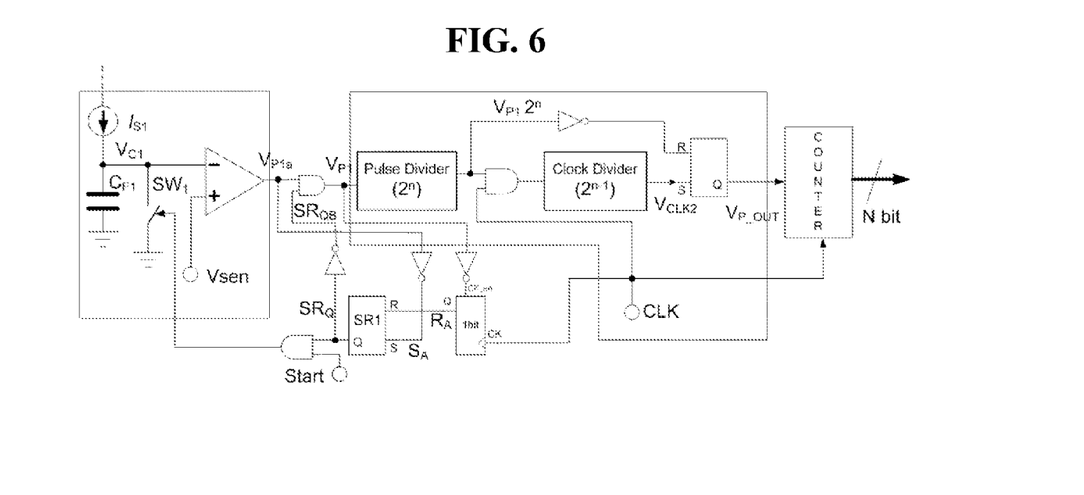
FIG. 6 is a modified example of FIGS. 3 and 4.

FIG. 6 is a modified example of FIGS. 3 and 4. That is, FIG. 6 is an example obtained by modifying a circuit in which the circuit of FIG. 3, the circuit of FIG. 4, and the counter unit 50 are connected to each other.

Figure 7:
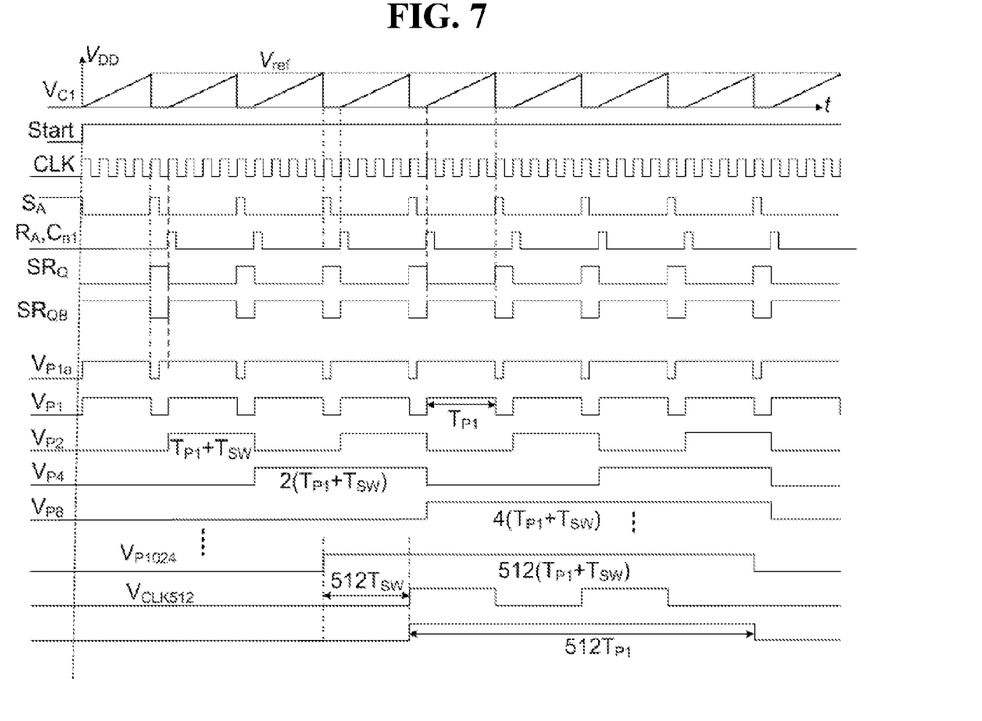
FIG. 7 is a voltage graph in a circuit of FIG. 6.

FIG. 7 is a voltage graph in the circuit of FIG. 6.

An advantage of the circuit of FIG. 6 is to have a pulse width of $512T_{P1}$ in which $T_{SW}$ is removed from an output voltage $V_{P\_OUT}$. That is, the circuit removing the unnecessary time factors (the switching time and the clock delay time) contained in the final pulse width is inserted, such that the pulse width generated from the pulse generating unit 30 is accurately amplified by the integer times, thereby making it possible to improve accuracy.

Therefore, the circuit of FIG. 6 may be said to additionally include the circuit removing 'components except for the pulse width of the output of the pulse generating unit 30' from the output pulse of the divider 40. In this case, the pulse generating unit 30 of the circuit of FIG. 6 needs to periodically generate the pulse having the pulse width which is proportional to the output voltage value of the S/H unit 20.

A digital value measured in the clock unit by the counter unit 50 is stored in a memory element (e.g., a register).

The sensor device according to the present invention has an advantage in that resolution is increased, but has a disadvantage in that a measurement time is increased. As a result, there is a disadvantage that a voltage change according to a time change may not be accurately represented.

FIG. 7 illustrates a timing diagram for the circuit of FIG. 6. When the start signal ("Start") converts from L to H (from Low to High voltage), operation begins of the circuit begins. Although the clock ("CLK") is illustrated by an exaggeratedly large time interval (large period), the clock actually has a very high frequency in practice. There are some small timing delay errors (Td, not shown) due to the clock interval, but these are relatively small compared to the switching delay Tsw.

In FIG. 7, the clock is shown with a period of about 1 microsecond to and the $V_{C1}$ rise time is about 3.5 microseconds. Starting at the left side of the graph, when the Start signal goes High, the voltage $V_{C1}$ starts ramping up at a constant slope. When the $V_{C1}$ is greater than $V_{ref}$, then the output voltage of the comparator, $V_{P1a}$, changes from High to Low (H to L). This change may also occur when $V_{C1}$ reaches and is equal to $V_{ref}$, depending upon the exact circuit.

Output $V_{P1a}$ feeds into one input of a AND gate. Output $SR_{QB}$ feeds into a second input of the AND gate. $SR_Q$ is the output of set-reset (SR) flip-flop (F/F) SR1 at the bottom of FIG. 6, and this output goes through an inverter to become $SR_{QB}$. The output $V_{P1}$ of the AND gate feeds into the $2^n$ pulse divider. The $2^n$ pulse divider may be alternately described as a "frequency divider" (because the pulse width is increased and the frequency is decreased). However, the term "pulse divider" is consistently used in this specification and claims as meaning that the pulse width is increased.

When the $V_{P1a}$ signal changes from H to L, the output of the SR F/F goes from L to H (input L to H in SR F/F input SA).

If the output of SR F/F is H, it turns the $SW_1$ switch on, it makes $V_{C1}$ into 0 voltage (Low). The output voltage of the comparator, $V_{P1a}$, is again converted from L to H (it stays as low for a brief moment and then turns back from L to H). At this time, the output of the SR F/F stays H.

Even $V_{P1a}$ changes from L to H, the output of SR F/F stays H. At this time, the output of the SR F/F is input to the AND gate through the NOT gate and $V_{P1}$ stays L.

If a Low signal is feed to the enable input of the 1 bit counter (shown at the lower middle of FIG. 6), then $V_{P1}$ generates H output at 1 cycle of the clock. Depending on the timing of the enable signal and the clock signal, it may not output H at the one cycle time. That is, it may be slightly smaller or larger than one cycle.

When output $R_A$ of the one bit counter is High, then output ($SR_Q$) of SR F/F SR1 converts from H to L. At this time, $V_{P1}$ becomes H. As a result, $V_{P1}$ has a low time of almost one cycle and an output H time of the comparator). As a result, after one cycle the $SW_1$ switch is turned off, so that $V_{C1}$ again starts to increase in voltage.

In summary, this circuit has a switch-on time for one cycle of the clock, amplifies the $V_{P1}$ and the clock by the divider, removes the unnecessary signal, and inputs the clock into the counter to generate an Nbit output.

Figure 8:
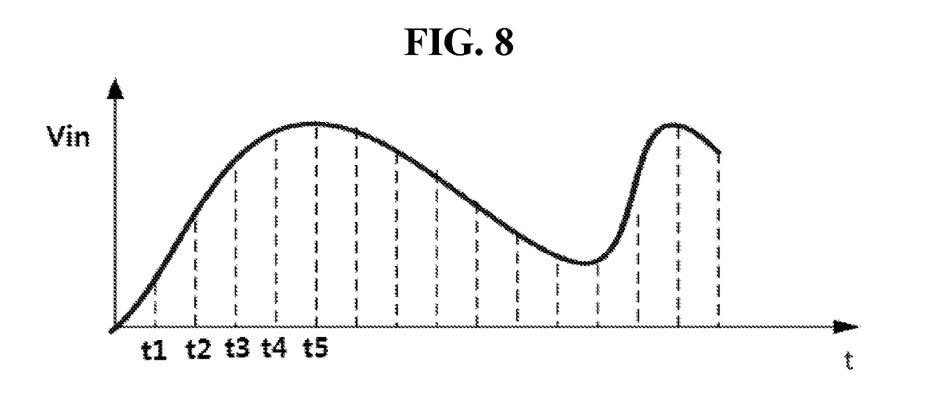
FIG. 8 is an example of an output voltage of a sensing voltage generating unit.

FIG. 8 is an example of the output voltage of the sensing voltage generating unit.

The output voltage Vin of the sensing voltage generating unit 10 is changed over time. It is preferable to sense the voltage at a short time interval in order to accurately measure the voltage change according to the time change, but there is a problem that a voltage sense at another timing (t=t2) may not start before the voltage sense at one timing (e.g., t=t1) is completed.

If the sampled voltage values are processed in parallel with each other, the above-mentioned problem may be solved.

Figure 9:
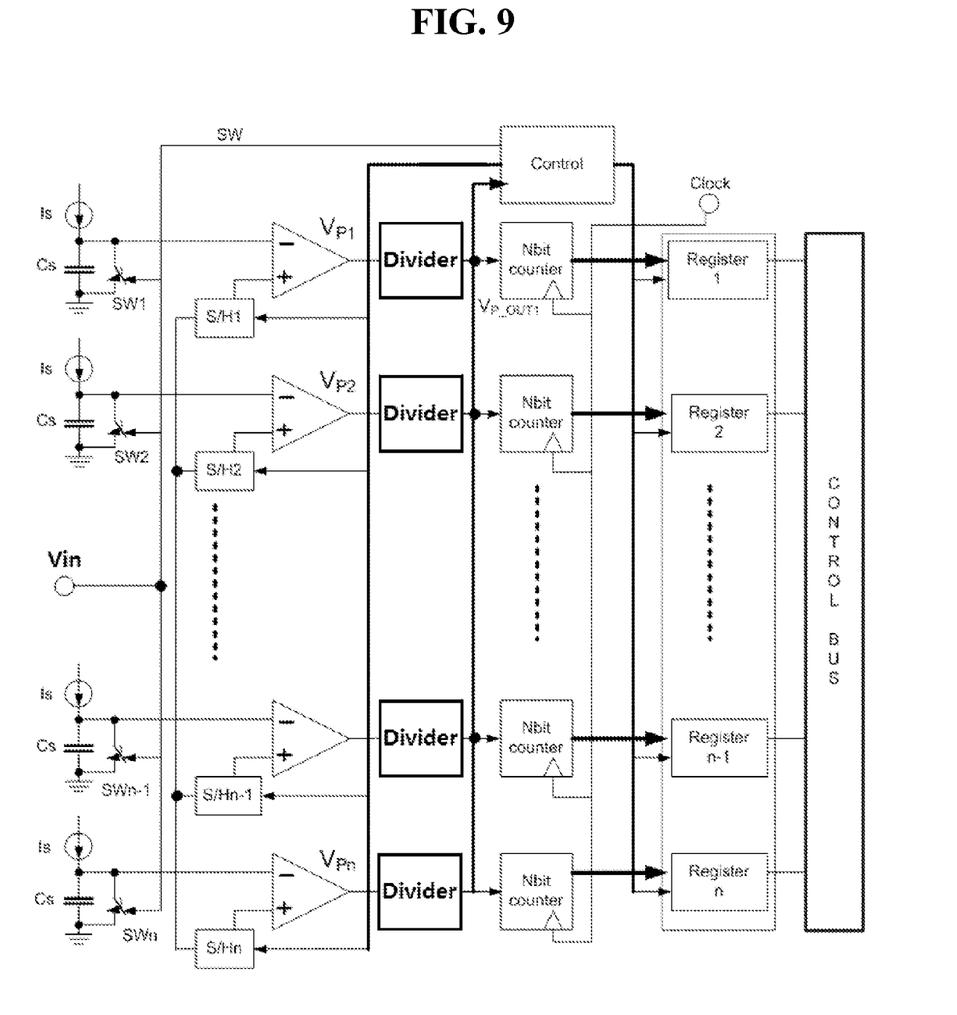
FIG. 9 is an example of a parallel fast transforming circuit.

FIG. 9 is an example of a parallel fast transforming circuit.

Since the circuit of FIG. 9 includes n S/H units 20, n pulse generating units 30, n dividers 40, and n counter units 50, the circuit may sense the voltage at a time interval which is denser n times than the case in which one S/H unit 20, one pulse generating unit 30, one divider 40, and one counter unit 50 are provided. Therefore, the voltage change according to the time change may be accurately represented.

In other words, the sensor device according to the present invention includes two or more S/H units 20, pulse generating units 30, dividers 40, and counter units 50, the sensing voltage generating unit 10 is connected to the two or more S/H units 20, and the output voltages of the respective S/H units 20 are connected to the pulse generating units 30, the dividers 40, and the counter units 50 which are different from each other, such that the parallel processing of the voltage sense may be enabled.

A sensing method according to the present invention, which is a sensing method using a sensor device including a sensing voltage generating unit 10, an S/H unit 20, a pulse generating unit 30, a divider 40, and a counter unit 50, includes the following operations.

First operation: an operation of outputting, by the sensing voltage generating unit 10, different voltage values depending on an external environment.

Second operation: an operation of storing and then outputting, by the S/H unit 20, a voltage value of a specific instant of an output voltage of the sensing voltage generating unit 10

Third operation: an operation of generating, by the pulse generating unit 30, a pulse having a period which is proportional to an input voltage value.

Fourth operation: an operation of dividing, by the divider 40, an output of the pulse generating unit 30.

Fifth operation: an operation of measuring, by the counter unit 50, a length of an output pulse of the divider 40 in a clock unit.

In the sensing method according to the present invention, in the case in which the input voltage of the S/H unit 20 is not changed for a predetermined time or more, the second operation may be removed.

Since the value measured in the clock unit in the fifth operation, which is a digital value, needs to be stored in a memory element (e.g., a register), the sensing method according to the present invention may further include the following sixth operation.

Sixth operation: an operation of storing, by the register, the value measured in the clock unit.

According to the exemplary embodiments of the present invention, the sensor device including the ADC using the pulse width modulation technology is the miniature device and has high resolution, thereby making it possible to measure a very small change in the value.

What is claimed is:
1. A sensor device comprising:
a sensing voltage generating unit receiving an input voltage and generating a sensed voltage that is a function of an external environment;

a pulse generating unit generating a first pulse having a first period, wherein the first period includes a first component that is proportional to the sensed voltage and a second component that is caused by a switching error of the pulse generating unit;

a first AND gate receiving the first pulse, receiving a processed clock signal, and outputting a second pulse;

a $2^n$ pulse divider receiving the second pulse and generating a third pulse that is approximately $2^n$ times longer than the second pulse;

a second AND gate receiving the third pulse, receiving a clock signal, and generating a fourth pulse;

a $2^{n-1}$ clock divider receiving the fourth pulse and generating a fifth pulse that is proportional to the switching error;

an inverter receiving the third pulse and generating a sixth pulse;

a reset-set (RS) flip-flop receiving the fifth pulse into a Set input, receiving the sixth pulse into a Reset input, and outputting a seventh pulse, wherein the seventh pulse is not proportional to the switching error; and a counter receiving the seventh pulse and outputting an N-bit value of the seventh pulse.

\* \* \* \* \*